United States Patent [19]

Lim et al.

[11] Patent Number: 4,924,099

[45] Date of Patent: May 8, 1990

[54] METHOD AND APPARATUS FOR MONITORING A FLOWSTREAM

[75] Inventors: Git B. Lim; Ronald E. Nieman, both of Calgary, Canada; Sanjoy Banerjee, Santa Barbara, Calif.

[73] Assignee: Exxon Production Research Company, Houston, Tex.

[21] Appl. No.: 296,398

[22] Filed: Jan. 9, 1989

Related U.S. Application Data

[63] Continuation of Ser. No. 941,972, Dec. 15, 1986, abandoned.

[51] Int. Cl.⁵ .............................................. G01V 5/00
[52] U.S. Cl. ............................... 250/390.04; 250/270
[58] Field of Search .................... 250/390.04, 390.05, 250/390.01, 252.1, 269, 270

[56] References Cited

U.S. PATENT DOCUMENTS

| | | | |
|---|---|---|---|
| 2,567,057 | 9/1951 | Krumrine | 250/391 |
| 2,873,377 | 2/1959 | McKay | 250/252.1 |
| 2,948,810 | 8/1960 | Caldwell et al. | 376/166 |
| 3,497,692 | 2/1970 | Mills, Jr. | 250/392 |
| 3,508,047 | 4/1970 | Mott et al. | 250/390 C |
| 3,508,052 | 4/1970 | Seevers | 376/165 |
| 3,710,112 | 1/1973 | Caldwell et al. | 376/164 |
| 3,805,079 | 4/1974 | Higatsberger et al. | 250/390 C |
| 4,028,267 | 6/1977 | Christell et al. | 250/390 C |
| 4,066,892 | 1/1978 | Givens | 376/165 |
| 4,190,768 | 2/1980 | Arnold et al. | 376/159 |
| 4,200,789 | 4/1980 | Arnold et al. | 376/159 |
| 4,209,695 | 6/1980 | Arnold et al. | 376/159 |
| 4,239,965 | 12/1980 | Oliver et al. | 250/270 |
| 4,264,812 | 4/1981 | Randall | 250/252.1 |
| 4,266,132 | 5/1981 | Marshall | 250/359.1 |
| 4,268,754 | 5/1981 | Srapeniants et al. | 250/390 C |
| 4,314,155 | 2/1982 | Sowerby | 250/390 C |

OTHER PUBLICATIONS

Knoll, Glenn F., *Radiation Detection and Measurement*. Pub: John Wiley & Sons: New York. Copyright 1979, pp. 26-33.

*Primary Examiner*—Janice A. Howell
*Assistant Examiner*—Richard Hanig
*Attorney, Agent, or Firm*—Richard F. Phillips

[57] ABSTRACT

A method and apparatus utilizing inelastic neutron scattering for measuring the volume fractions of the various constituents of a multiconstituent substance. A source of fast neutrons is positioned proximate the substance. A detection system is provided to monitor the gamma emissions resulting from inelastic scattering of the fast neutrons from the various nuclides within the substance. The resulting measurement of the relative abundance of gamma emissions characteristic of the various nuclides within the substance is used to determine the relative concentrations of the major constituents of the substance. In a preferred embodiment, the present invention is used to provide a real-time measurement of the volume fractions of oil, gas and water in the production flowstream from an oil well.

8 Claims, 5 Drawing Sheets

METHOD AND APPARATUS FOR MONITORING A FLOWSTREAM

This application is a continuation application of co-pending application Ser. No. 941,972, filed on Dec. 15, 1986.

TECHNICAL FIELD

The present invention relates generally to systems for monitoring fluids within an enclosure. More specifically, the present invention relates to a method and apparatus utilizing inelastic neutron scattering for measuring the volume fractions of the various constituents of a multiconstituent flowstream within a conduit.

BACKGROUND OF THE INVENTION

Production from most oil wells takes the form of a multiconstituent flowstream. For a typical oil well this flowstream includes crude oil, brine, hydrocarbon gases, various inorganic gases, and minor amounts of particulate matter. The fractional representation of each constituent of the production flowstream varies from well to well, and even for a single well can vary significantly over time. It is often necessary to maintain data on the rate at which each of the flowstream constituents is produced for one or more wells in a reservoir. This information is useful in monitoring the effectiveness of the reservoir production scheme, detecting faults in the production equipment for an individual well, adjusting the equipment used for separating the produced fluids collected from groups of wells, and in determining royalty payments for produced hydrocarbons.

The earliest methods for determining the fractional representation of the various fluids within the flowstream of an oil well relied on manual sampling and analytical procedures. A representative sample of the flowstream was collected and through physical separation and chemical analysis the fractional representation of each constituent was determined. Manual analysis is still used today in many instances, particularly where accuracy is particularly important. However, manual testing is relatively expensive, particularly in remote oil fields or where frequent updating is necessary. Further, collecting small volume samples which accurately represent the flowstream is difficult, especially in high pressure, high temperature production systems.

Automated flowstream analysis systems have been developed to avoid much of the expense associated with manual testing. These automated systems typically rely on gravity driven physical separation of the constituents of the flowstream. Such systems are not accurate for applications where the flowstream includes an oil-water emulsion, which cannot be gravity separated. Such systems are also of limited use for heavy oil reservoirs, where the density difference between the produced oil and brine is too small to provide significant driving force for gravity separation. Gravity driven automated analysis systems also tend to be bulky, expensive, and require careful maintenance.

To avoid many of the disadvantages of traditional methods of flowstream analysis, monitoring systems have been developed which are based on interactions between the flowstream and a population of neutrons introduced into the flowstream. The general principle of operation of neutron type monitoring systems is that by detecting the frequency with which characteristic neutron-nuclide reactions occur, the relative abundance of various elements within the flowstream can be determined. From this data it is possible, knowing the elemental composition of the various constituents of the flowstream, to derive the fractional representation of each constituent of the flowstream. Since neutrons and the gamma radiation resulting from the interaction of neutrons with matter are only slightly attenuated in passing through a metallic conduit, the neutron source and the various detectors can be positioned external to the conduit. This avoids the need to withdraw a representative sample of the flowstream or position a monitor in physical contact with the flowstream, as is necessary in other methods of analysis.

Though neutron type monitoring systems provide significant advantages over traditional methods of flowstream analysis, the various neutron type monitoring systems developed heretofore are subject to limitations which greatly restrict their use in oil field applications. These limitations are best appreciated by considering the principles of operation of two classes of neutron monitoring systems familiar to those skilled in the art.

One class of neutron based flowstream monitors is illustrated by U.S. Pat. No. 4,190,768, issued Feb. 26, 1980. An oil, gas and water mixture within a pipeline is exposed to a neutron population. The neutrons are moderated (thermalized) by the hydrogen and carbon nuclides within the fluid. A portion of the thermal neutrons are captured by the constituent nuclides of the fluid. Each neutron capture event results in the emission of a prompt gamma photon having an energy characteristic of the nuclide. By monitoring the gamma ray emissions characteristic of the reactions $H^1(n,\gamma)H^2$, $S^{32}(n,\gamma)S^{33}$, and $Cl^{35}(n,\gamma)Cl^{36}$ the fractional amounts of crude oil, water and gas within the fluid can be determined. This method is disadvantageous in that it is dependent upon a precise knowledge of the concentration of sulphur within the oil for quantifying the amount of crude oil present. This requires a continuous, separate chemical analysis. Further, because the method relies on thermal neutron capture, it requires that the source neutrons be moderated. Where the conduit contains a significant quantity of hydrogenous fluid this does not pose a problem. However, where the conduit is small or the fluid is predominantly gas, supplemental moderation must be provided.

An alternate neutron based fluid monitoring system is set forth in U.S. Pat. No. 2,567,057, issued Sept. 4, 1951. In this system a collimated beam of fast or epithermal neutrons is directed into a conduit. A neutron detector is positioned to monitor the degree of attenuation of the neutron flux resulting from neutron capture or scattering. The fractional decrease in the flux can be related to the composition of the sample. This system is useful in measuring changes in the composition of simple non-gaseous fluid, but is not useful where a significant amount of gas is present in the sample. Additionally, the accuracy of this method diminishes significantly at sample thicknesses greater than one or two centimeters. This precludes use of this system "in-situ" in oil field applications, where production conduits have inside diameters generally well in excess of 5 cm. This system is further disadvantageous in that it cannot distinguish between oil and water.

It would be desirable to develop a neutron based monitoring system which could be used in conjunction with unmodified production equipment to determine the composition of oil field production flowstreams. It would be further desirable if this system does not rely on the detection of trace impurities for distinguishing between oil and water and can be used to accurately monitor fluids over a wide range of gas, water, and oil fractions.

SUMMARY OF THE INVENTION

A method and apparatus are set forth which are useful for monitoring the relative concentrations of the various constituents of a multiconstituent flowstream. A substantially unmoderated neutron source is positioned proximate the flowstream. The gamma emissions resulting from inelastic scattering interactions between high energy neutrons and the nuclides within the flowstream are monitored by a detection system. A measurement of the relative abundance of gamma emissions characteristic of the various nuclides within the flowstream is used to determine the relative concentrations of each constituent of the flowstream.

In a preferred embodiment, the fluid monitoring system of the present invention is tailored for use in monitoring the relative volume fractions of oil, gas and water in the production flowstream of an oil well. The gamma spectrum resulting from exposing the flowstream to a fast neutron flux is monitored for the characteristic gamma radiation resulting from inelastic neutron scattering from $H^1$ and $C^{12}$ nuclides within the flowstream. This data is related to calibration information for the system to yield the oil, gas and water fractions of the sample. In the preferred embodiment an isotopic neutron source substantially free from beryllium is employed to prevent interference with the measurement of the characteristic inelastic scattering gamma emissions of $C^{12}$.

The present invention is particularly advantageous in that it is non-intrusive and requires no modification to the conduit carrying the flowstream. The present invention is further advantageous in that it is not dependent on a measurement of trace impurities within the flowstream, does not require the use of a neutron generator, and is readily transportable.

BRIEF DESCRIPTION OF THE DRAWINGS

For a better understanding of the present invention, reference may be had to the accompanying schematic and graphs, in which.

These figures are not intended as a definition of the invention, but are provided solely for the purpose of illustrating preferred embodiments of the invention.

DESCRIPTION OF THE PREFERRED EMBODIMENTS i. General Principles of the Invention

Figure 1:
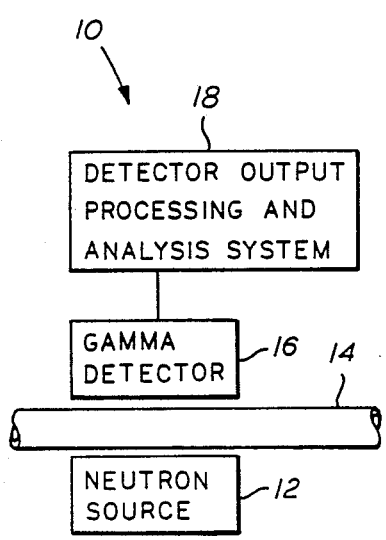
FIG. 1 is a schematic drawing of the source, detector and signal processing system of the present invention.

FIG. 1 provides a schematic illustration of a fluid monitoring system 10 incorporating a preferred embodiment of the present invention. The principal components of the fluid monitoring system 10 are: a source 12 of fast neutrons positioned adjacent the conduit 14 carrying the flowstream of interest; a gamma detector 16 positioned near the conduit 14 to monitor the gamma spectrum resulting from inelastic neutron scattering as the fast neutrons interact with the flowstream; and, a signal processing and analysis system 18 which receives the output of the detector 16 and develops data from which the relative volume fractions of the principal flowstream constituents can be determined. Though the preferred embodiment of the fluid monitoring system 10 has been developed for use in monitoring the fractional representation of oil, water and gas in the production flowstream of an oil well, the present invention is not limited to this application. Those skilled in the art will recognize that the principles of the present invention can be applied in monitoring coal moisture, in well logging and in many other applications. To the extent that the following description is specific to monitoring oil well production flowstreams, this is by way of illustration rather than limitation.

The present invention is based in part on our discovery that for certain applications, neutron type fluid composition monitoring systems should be based on the detection and analysis of fast neutron interactions with the various nuclides in the flowstream, rather than on thermal neutron interactions. The preferred embodiment of the present invention relies on measurement of the inelastic scattering of fast neutrons passing through an oil well production flowstream to establish the relative volume fractions of oil, water and gas within the flowstream. This is accomplished by monitoring the gamma spectrum emanating from the flowstream to establish the abundance of the characteristic gamma photons resulting from the following inelastic scattering reactions:

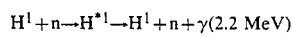

$H^1 + n \rightarrow H^{*1} \rightarrow H^1 + n + \gamma(2.2\ MeV)$

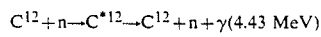

$C^{12} + n \rightarrow C^{*12} \rightarrow C^{12} + n + \gamma(4.43\ MeV)$

As more fully detailed below, this data, coupled with information data regarding the nature of the oil produced from the well, is sufficient to permit accurate determination of the relative volume fractions of oil, water and gas within the flowstream.

ii. Physical Components of the Monitoring System

The preferred neutron source 12 for use in the present invention is a $C^{13}$-$Pu^{238}$ isotopic chemical source having an activity on the order of 5 Curies. However, a $C^{13}$-$Ac^{227}$ source or any other isotopic neutron source which does not have a significant gamma yield at 2.2 MeV or 4.43 MeV (the gamma energies characteristic of inelastic neutron scattering from $H^1$ and $C^{12}$) could be used instead. Careful source selection is important because most commercially available isotopic neutron sources generate neutrons through an $\alpha$-$Be^9$ reaction, which yields a 4.43 MeV gamma peak of sufficient magnitude to mask the 4.43 MeV peak resulting from inelastic neutron scattering from the $C^{12}$ nuclides in oil. A neutron generator could be used instead of an isotopic source. However, because neutron generators are very expensive and require regular maintenance it will generally be preferable to use an isotopic neutron source.

Since the present invention utilizes fast rather than thermal neutrons, the amount of thermalizing material intermediate the source 12 and the conduit 14 should be minimized. Further, to avoid interfering with the measurement of neutron interactions with the $H^1$ and $C^{12}$ nuclides within the flowstream, it is desirable to minimize the amount of hydrogenous and carboniferous material external to the conduit 14 in the vicinity of the source 12 and detector 16. This is primarily of concern regarding source shielding and conduit insulation. To the extent that shielding or insulation is necessary, the shielding or insulating material should not incorporate amounts of hydrogen or carbon in the vicinity of the source 12 or detector 16.

The detector 16 is preferably a Bicron 7.5 cm x 7.5 cm sodium-iodide crystal scintillation detector equipped with an appropriate photomultiplier tube. Obviously, a lithium drift germanium detector or other gamma detector providing an output proportional to the strength of each detected gamma photon could be substituted. Details of these detectors and the associated multichannel signal processing systems 18 are well known to those skilled in the art. As shown in FIG. 1, the detector 16 and neutron source 12 should be positioned as close as practical to the conduit 14. Where the conduit 14 is horizontal, the source 12 and detector 16 should be oriented so that their centerpoints define a vertical line passing through the central axis of the conduit 14 with the source 12 on the underside of the conduit 14 and the face of the detector 16 directly above the conduit 14. This arrangement maximizes the count rate observed by the detector 16 and minimizes data aberrations resulting from varying flow regimes within the conduit 14. Where the flowstream is at a very high temperature it may be necessary to space the source 12 and detector 16 a short distance radially outward from the conduit 14. The neutron source 12 and detector 16 should be firmly secured in the desired positions relative to the conduit 14 by a rigid mounting frame. This is important because minor changes in geometry can introduce significant error into the measurements. Where variations in flow regime within the conduit 14 are significant, it may be desirable to utilize two sources 12, located directly above and directly below the conduit 14. With this arrangement the detector 16 would be positioned at the side of the conduit, equidistant from the two sources 12.

iii. Calibration and Use of the Monitoring System

In the preferred embodiment of the invention, empirical relationships between the flowstream composition and the observed gamma radiation count rate in selected energy ranges are used to calculate the volume fractions of oil, gas and water present in the flowstream. These empirical relationships are derived experimentally by securing the source 12 and detector 16 in fixed orientation to a conduit identical to the conduit 14 used to transport the production flowstream. Various combinations of oil, water and gas in precisely measured quantities are placed within the conduit, and for each such combination the resulting count rates at the 2.2 MeV gamma peak for $H^1$ inelastic neutron scattering and at the 4.43 MeV gamma peak for $C^{12}$ inelastic neutron scattering are recorded. As more fully set forth below, this data is then used to develop a calibration of the system 10 from which the composition of an actual production flowstream can be determined. Of course, it would be possible to develop a theoretical rather than empirical basis for determining the oil, gas and water volume fractions in a production flowstream, thus avoiding the need for the calibration tests detailed below. However, due to the many variables inherent in the system (source-conduit-detector geometry, detector efficiency, flowstream contaminants, etc.) this would be a formidable task and would possibly yield results less accurate than those obtained experimentally.

A trial calibration of the preferred embodiment was conducted using static mixtures of bitumen, water, and air to model production flowstreams encountered at the Cold Lake Tar Sands Reservoir in Alberta, Canada. The monitoring system 10 of the present invention is particularly well suited for use in this application because the difficulty in handling the high temperature, bituminous flowstream resulting from tar sands production wells greatly complicates monitoring by traditional automated or manual methods. The non-intrusive, in-situ monitoring provided by the present invention avoids these difficulties.

Figure 3:
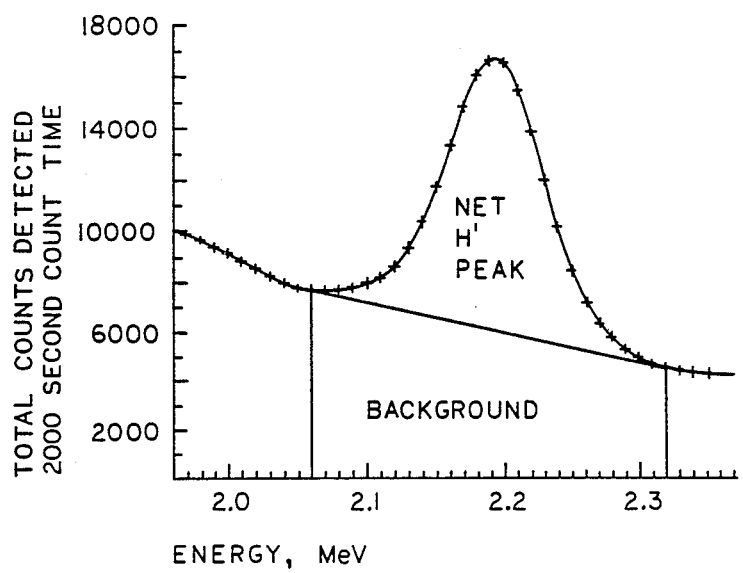
FIG. 3 illustrates the definition of the net $H^1$ inelastic neutron scattering gamma peak.
Figure 2:
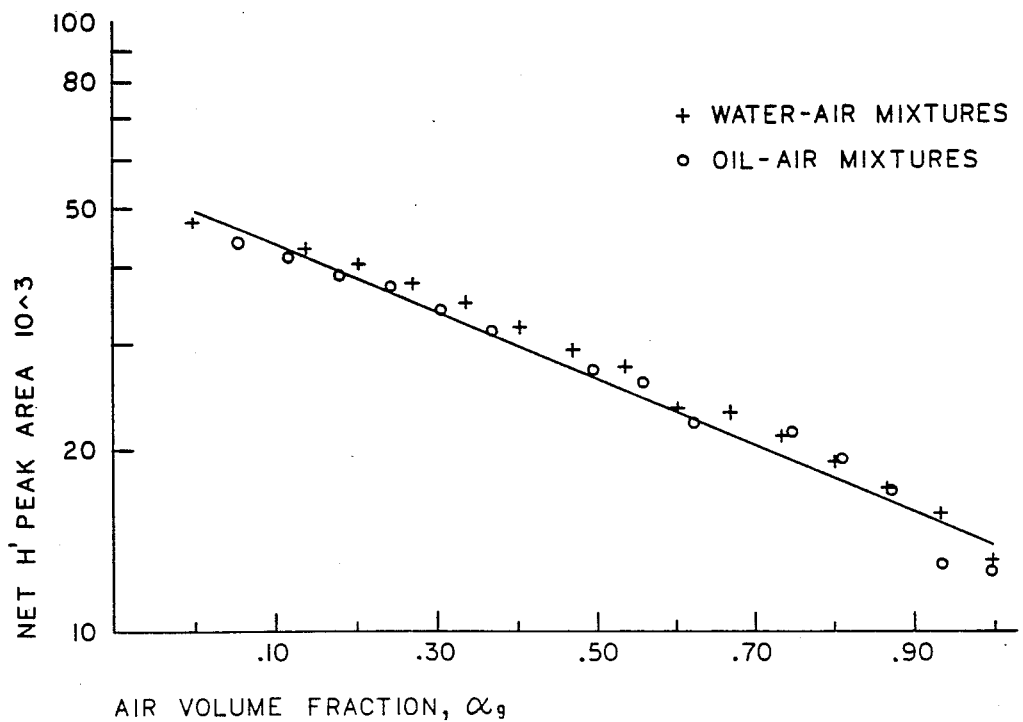
FIG. 2 is a graph showing net magnitude of the $H^1$ inelastic scattering gamma peak as a function of air concentration for water-air and bitumen-air mixtures.
Figure 4:
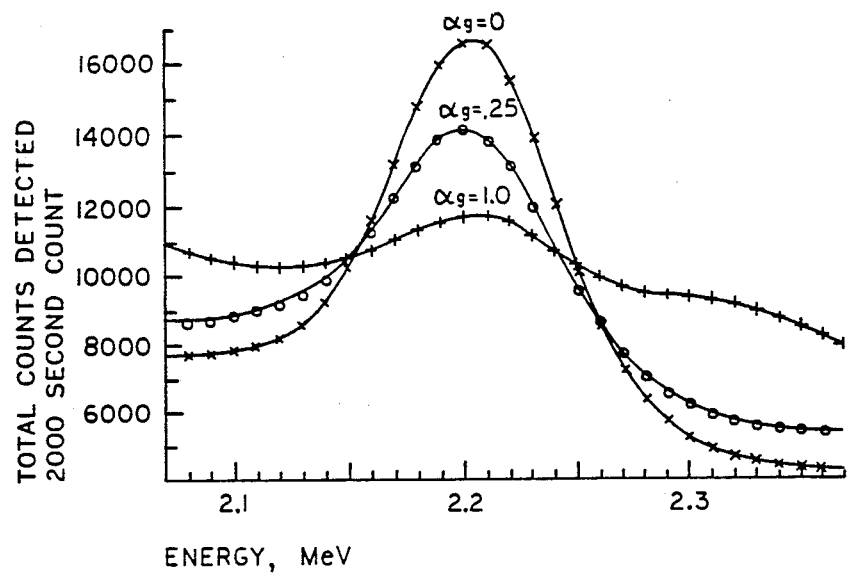
FIG. 4 illustrates the shape of the $H^1$ inelastic neutron scattering gamma peak for three different water-air mixtures.

Initially, the monitoring system 10 was set up with the source 12 and detector 16 rigidly secured to a section of 15 cm inside diameter steel conduit 14 in the arrangement illustrated in FIG. 1. After setup of the system 10, the first step in the calibration was to establish the empirical relationship between the magnitude of the 2.2 MeV gamma peak and the gas content of the conduit 14. To accomplish this, the conduit 14 was filled with a range of water-air mixtures. The gamma count rate for inelastic neutron scattering from $H^1$ nuclides was recorded for each. This procedure was then repeated for various proportions of Cold Lake bitumen and air. Because handling pure bitumen is difficult, the bitumen was combined with 15% by volume of light end condensate as a diluent. FIG. 2 gives the results obtained from this trial. It can readily be seen that the relationship between the net count rate and air fraction for bitumen and water are substantially identical. This correlates with the fact that Cold Lake bitumen and water have substantially identical hydrogen concentrations per unit volume. The net $H^1$ inelastic neutron scattering gamma peak is based on the gross peak minus the interpolated background, as illustrated in FIG. 3. The relationship between the peak shape and void fraction within the conduit 14 is given in FIG. 4. It is believed that the decrease in the net background count rate with increases in the liquid content of the conduit 14 results from the shielding provided by the liquid.

From the data shown in FIG. 2, regression analysis was used to establish the following equation relating the gas volume fraction ($\alpha_g$) to the magnitude of the net hydrogen peak ($\Delta A_h$):

$$\alpha_g = 8.0911 - 0.7465 \ln (\Delta A_h) \qquad \text{eqn. 1}$$

The second step in the calibration of the system 10 was to determine the effect of water and bitumen on the gamma count rate in that portion of the gamma spectrum corresponding to inelastic neutron scattering with $C^{12}$ nuclides. This was accomplished by obtaining test data based on a range of water-air and bitumen-air mixtures in the same manner described above for determining $H^1$ inelastic neutron scattering data. Preferably, the $H^1$ and $C^{12}$ data for each test mixture are determined simultaneously.

Figure 5:
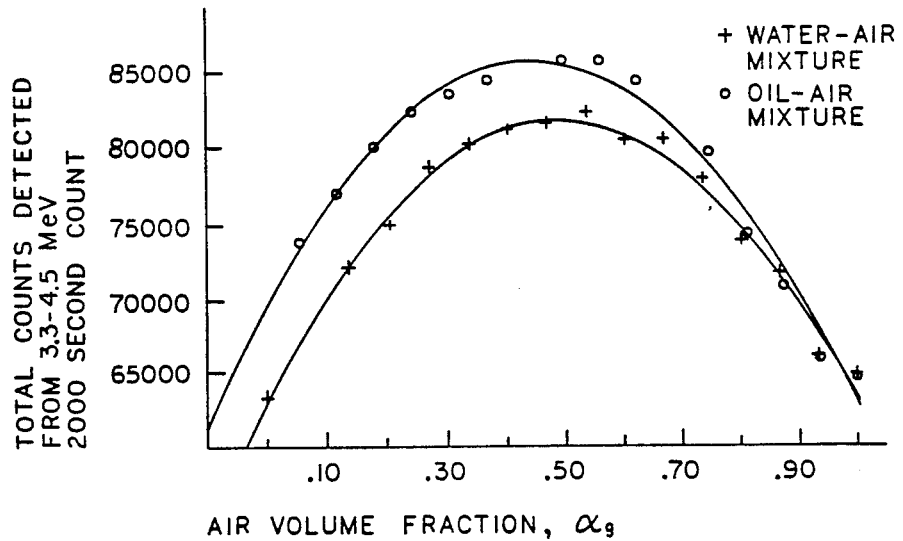
FIG. 5 illustrates the gross magnitude of gamma peak in the energy range of 3.3–4.5 MeV for a range of water-air and bitumen-air mixtures.

The data obtained in this second step of the calibration are set forth graphically in FIG. 5. The indicated count rates represent gross detected gamma photons over the energy range of 3.3–4.5 MeV. The net difference in count rate between the curve based on water concentration and the curve based on bitumen concentration represents that portion of the count rate attributable to inelastic neutron scattering from the $C^{12}$ nuclides. Carbon is, of course, present in the bitumen samples and absent from the water samples. A comparison of the two curves shows that the gamma spectrum strength in the energy range of interest is strongly affected by factors other than carbon concentration. It is believed that the increasing count rate as the air fraction is decreased from 1.00 to about 0.45 results from increasing Compton-downscattering by water or bitumen of the abundant 6.1 MeV gamma flux generated by the neutron source. The decreasing count rate as the air fraction goes from 0.45 to 0 is believed to result from the shielding effect of the liquid becoming dominant over the Compton scattering at low gas volume fractions.

Figure 6:
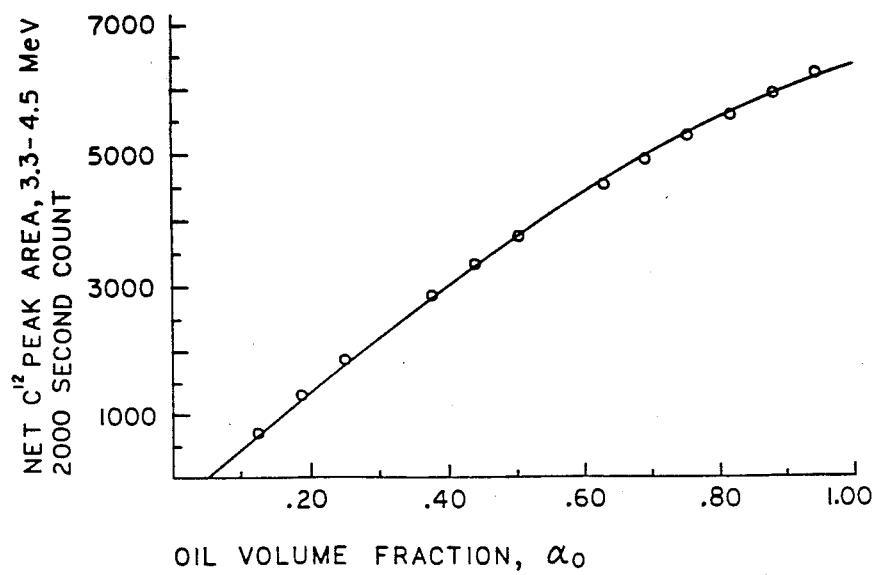
FIG. 6 illustrates the magnitude of that portion of the gamma peak attributable to $C^{12}$ inelastic neutron scattering as a function of bitumen volume fraction in a range of bitumen-air mixtures.

Using polynomial regression analysis of the test data, the $C^{12}$ gross count rate for bitumen-air mixtures ($A_o$) and water-air mixtures ($A_w$) can be related to the gas volume fraction and the $C^{12}$ gross count rate for air by the following expressions:

$A_w = [.9954 + 1.2591 \alpha_g - 1.403 \alpha_g^2 + .153 \alpha_g^3] A_{air}$ eqn. 2
$A_o = [1.0996 + 1.173 \alpha_g - 1.390 \alpha_g^2 + .111 \alpha_g^3] A_{air}$ eqn. 3
where $A_{air}$ = the gross count rate from 3.4 to 4.5 MeV for $\alpha_g = 1.00$ The net difference between the air-water and air-bitumen curves, representing the count rate attributable to inelastic neutron scattering from $C^{12}$ nuclides, is shown in FIG. 6 as a function of the oil volume fraction. Using polynomial regression analysis, this relationship can be approximated by the following equation:

$\alpha_o = .05546 + 5.419x + 35.55 x^2$ eqn. 4
where $X = (\Delta A_o)/(A_w)_1$
$\Delta A_o = A_o - A_w$ for the specified gas fraction
and $(A_w)_1 = A_w$ for $\alpha_g = 1.00$.

Having calibrated the system 10 through use of the procedure detailed above, the volume fractions of gas, oil and water in a production flowstream can be determined. The gross $C^{12}$ peak area, $A_c$, and the net $H^1$ peak area, $\Delta A_h$, are determined from the gamma spectrum obtained from the flowstream of interest. Equation 1 is applied to the net hydrogen peak area to yield the gas volume fraction, $\alpha_g$. Knowing the gas volume fraction, equation 2 is used to obtain the background $C^{12}$ peak, $A_w$, assuming the liquid volume fraction is entirely water. By subtracting this value of $A_w$ from the measured value of $A_c$, the net carbon peak area, $\Delta A_c$, for the flowstream is determined. This value is then used in equation 4 to determine the oil volume fraction, $\alpha_o$. The actual volume fraction of water, $\alpha_w$, is then determined from the relation:

$$\alpha_w = 1 - \alpha_g \alpha_o \qquad \text{eqn. 5}$$

Obviously, equations 1–4 are valid only for the system 10 as configured in the initial trial detailed above. However, using these calibration procedures equivalent empirical equations can be readily developed for similar embodiments of this invention. In the test detailed above the conduit 14 used to calibrate the system 10 was subsequently inserted into the production pipeline for monitoring of the production flowstream. In future applications of the present invention, however, it is anticipated that the production pipeline will not be altered and the calibration will be conducted using a length of conduit identical to the production pipeline.

In actual application of the present invention the signal processing and analysis system 18 would incorporate a microcomputer which would be provided with calibration data for the monitoring system. This microcomputer would automatically receive the $H^1$ and $C^{12}$ count rates and routinely calculate the current values for the volume fractions of gas, water, and oil.

Those skilled in the art will recognize the many advantages provided by the present invention in flowstream monitoring. The monitoring system is small and requires little set-up time. All calibrations can be conducted away from the well site. Thus, a single unit can be taken to the field for periodic monitoring of the flowstreams produced by many wells in a production unit. Further, the monitoring system is accurate over the full range of possible oil-water-gas volume fraction combinations and, being nonintrusive, is substantially unaffected by the pressure, temperature and flow regime conditions within the conduit.

iv. Alternate Calibration and Use of the Monitoring System

As will be readily appreciated by those skilled in the art, the principles of the present invention may be applied in other manners to obtain different processes from which the composition of a flowstream may be determined. In fact, many different embodiments of the invention may be practiced using a given source-conduit-detector configuration. For example, in the course of conducting experiments regarding the embodiment detailed above, it was discovered that an improvement in calculating the gas fraction of a flowstream can be obtained by relating the gas fraction to the magnitude of the sum of the $H^1$ inelastic scattering gamma peak and the inelastic scattering sumpeak for $H^1$ and $O^{16}$. A test calibration of the system 10 using this alternative embodiment of the present invention was conducted as follows.

Figure 7:
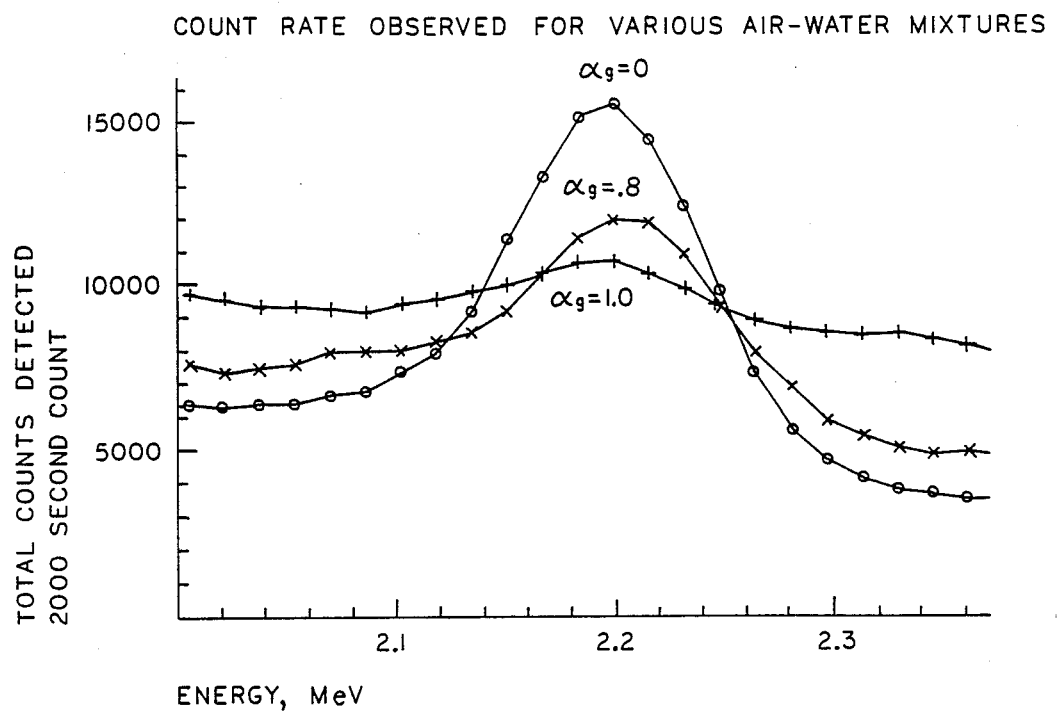
FIG. 7 illustrates the shape of the $H^1$ inelastic neutron scattering peak for three water-air mixtures as measured in the tests corresponding to the alternate embodiment of the invention.
Figure 8:
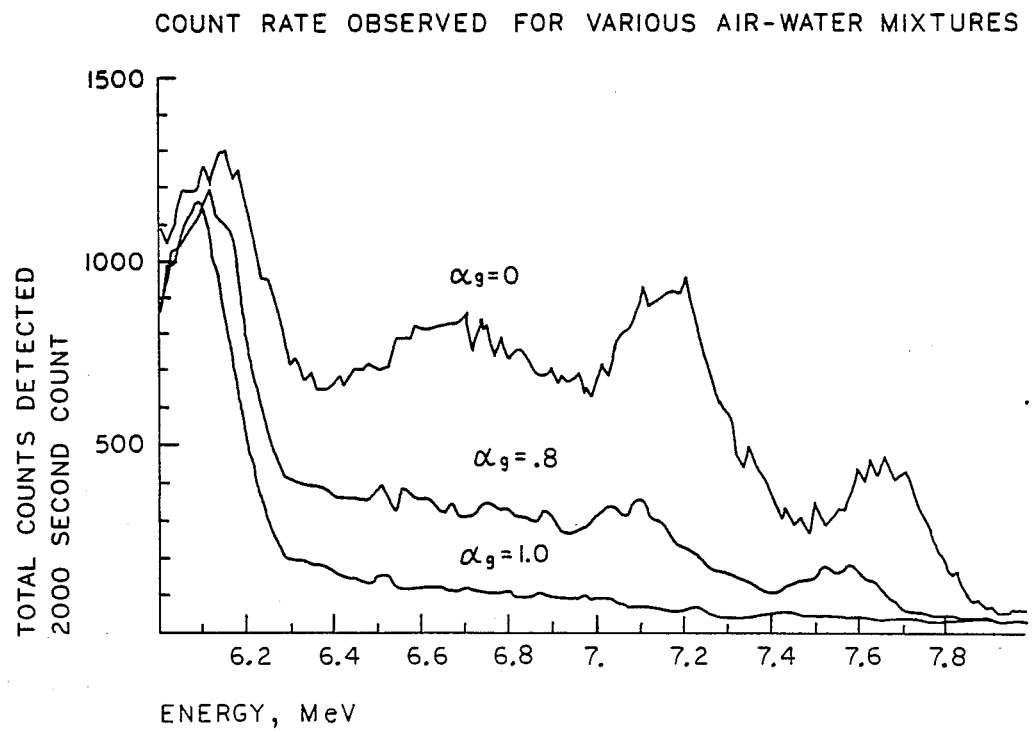
FIG. 8 shows the gamma spectrum over the energy range of 6.0–8.0 MeV for three water-air mixtures as measured in the tests corresponding to the alternate embodiment of the invention.
Figure 9:
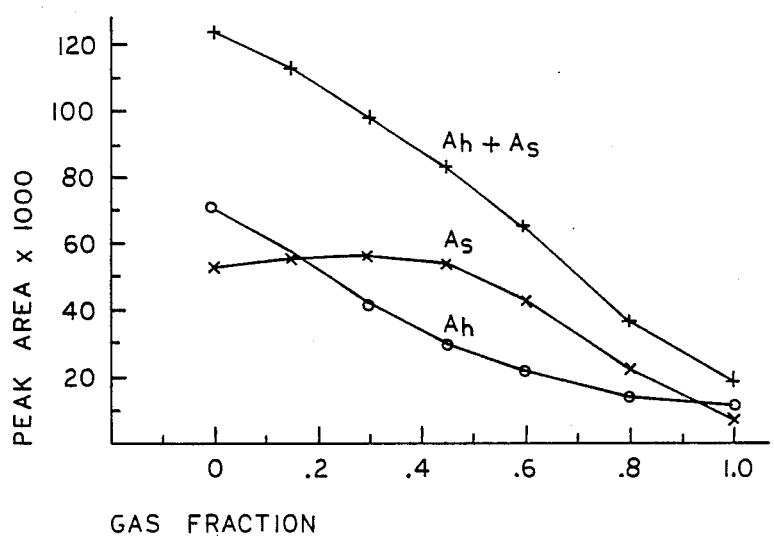
FIG. 9 shows the magnitude of the $A_s$, $A_h$, and $A_{hs}$ peaks as a function of gas fraction.

First, the conduit 14 was filled with a range of water-air mixtures. For each mixture, the gamma count rates were recorded both for inelastic neutron scattering with $H^1$ nuclides and also for the energy range of 6.4 to 8.0 MeV. The 6.4 to 8.0 MeV energy range is believed to represent the sumpeaks resulting from simultaneous detection of the 6.1 MeV gamma flux generated by the $C^{13}$-$Pu^{238}$ source and lower energy gammas resulting from other interactions, primarily inelastic neutron scattering from $H^1$ nuclides, between the neutrons and the liquid. The relationship between the gas fraction in the conduit 14 and the shape of the $H^1$ inelastic neutron scattering peak is given in FIG. 7. A corresponding relationship between the gas fraction and the shape of the peak in the 6.4 to 8.0 MeV gamma energy range is given in FIG. 8. FIG. 9 shows the magnitude of the net $H^1$ peak ($A_h$) and the magnitude of the integrated 6.4 to 8.0 MeV gamma Peak ($A_s$) as a function of gas fraction. It is readily observed from FIG. 9 that $A_h$ becomes increasingly less sensitive to changes in the gas fraction above a gas fraction of about 0.5 and that $A_s$ becomes relatively insensitive to changes in the gas fraction below a gas fraction of about 0.5. The sum of $A_h$ and $A_s$ (designated $A_{hs}$), also plotted on FIG. 9, exhibits excellent overall sensitivity to gas fraction changes over the whole range of gas fractions.

Figure 10:
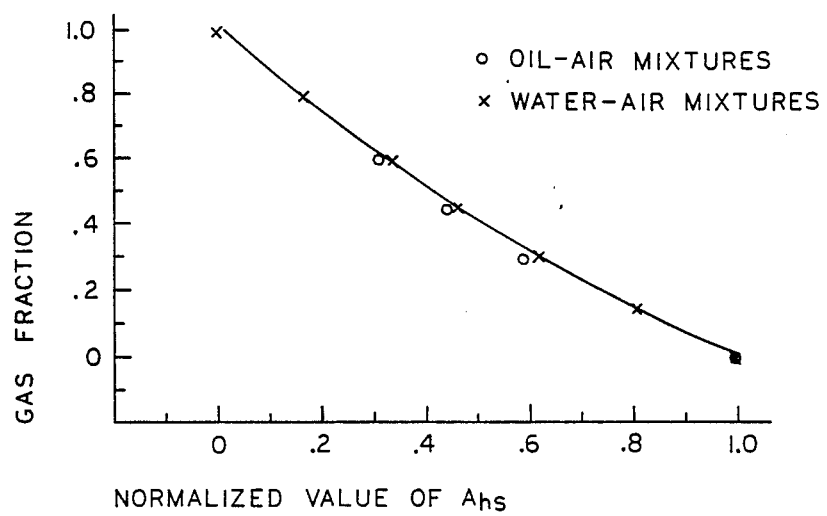
FIG. 10 shows the gas fraction as a function of the normalized value of $A_{hs}$ for a range of oil-air and water-air mixtures.

A similar test was conducted with the conduit filled with various proportions of oil and air. For convenience in testing, Esso Uniflo Motoroil was used. The results of this test and that detailed above for water and air were normalized and plotted in FIG. 10. Normalization was performed through application of the equation:

$$X_{hs} = \frac{R_{hs} - (R_{hs})_e}{(R_{hs})_f - (R_{hs})_e} \qquad \text{eqn. 6}$$

where
$X_{hs}$ is the normalized value of $A_h + A_s$;
$R_{hs} = A_{hs}/A_o$;
$A_o$ = gross magnitude of the $O^{16}$ inelastic neutron scattering peak in the energy range of 4.9–6.3 MeV; and
the subscripts "e" and "f" refer, respectively, to the conduit being empty and full of liquid.

This normalization eliminates any errors introduced as a result of electronics drift. It can readily be seen from FIG. 10 that the relationship between the normalized count rate and the gas fraction are substantially identical for water-air and oil-air mixtures. From the data shown in FIG. 10, regression analysis was used to establish the following equation relating the gas volume fraction ($\alpha_g$) to the magnitude of the normalized value of $A_{hs}$:

$$\alpha_g = 1.0081 - 1.3914 X_{hs} + 0.3875 (X_{hs})^2 \qquad \text{eqn. 7}$$

Figure 11:
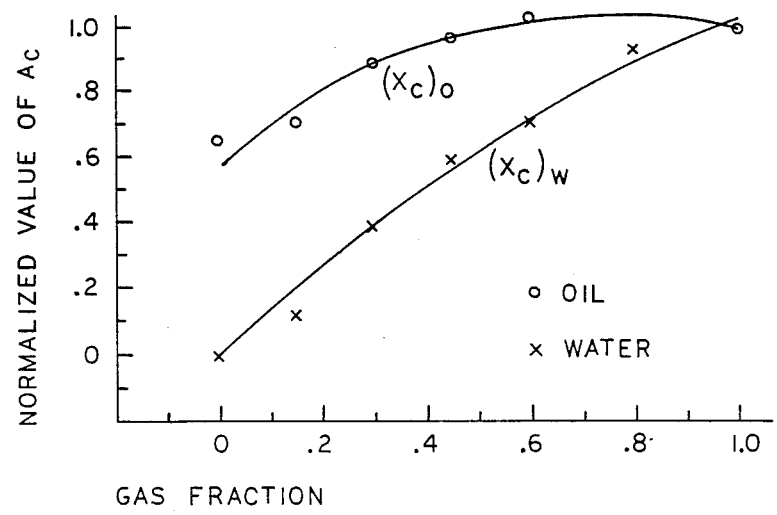
FIG. 11 shows the normalized value of $A_c$ as a function of gas fraction for oil-air and water-air mixtures.

The next step in the calibration was to establish the relationship between the oil and water content of the conduit and the $CX^{12}$ count rate. This was accomplished in substantially the same manner as was used in the embodiment detailed previously, with the only significant differences being that the energy window employed was 3.8 to 4.6 MeV and the count rate was normalized in a manner analogous to that used for normalizing $A_{hs}$. The relationships between the normalized count rate ($X_c$) in the $C^{12}$ window and the gas fraction for gas-water and gas-oil mixtures are given in FIG. 11. From the gas-water data, polynomial regression analysis was applied to yield the equation $$(X_c)_w = 1.447 \alpha_g - 0.417 \alpha_g^2 \qquad \text{eqn. 8}$$

The net difference in normalized count rate between the air-water and air-oil curves, representing that portion of the air-oil curve attributable to inelastic scattering from $C^{12}$ nuclides, can be approximated through the application of regression analysis by the equation:

$$\alpha_o = 1.496 \Delta X_c \qquad \text{eqn. 9}$$

where $\Delta X_c = (X_c)_o - (X_c)_w$.

Having calibrated the system through use of the procedure detailed above, the volume fractions of gas, oil and water in a production flowstream can be readily determined from the measured values of the $C^{12}$ peak, the $H^1$ peak and the $H^1$ plus $O^{16}$ sumpeak. The normalized value $X_{hs}$ is applied to equation 7 to yield the gas fraction, $\alpha_g$. Knowing $\alpha_g$, equation 8 is used to obtain the normalized background $C^{12}$ peak for a water-air mixture, $(X_c)_w$. By subtracting this value from the measured value of $X_c$, the net normalized carbon peak area, $\Delta X_c$, is determined. This value is then inserted in equation 9 to yield the oil volume fraction, $\alpha_o$. Equation 5 is then applied to yield the water volume fraction, $\alpha_w$.

Figure 12:
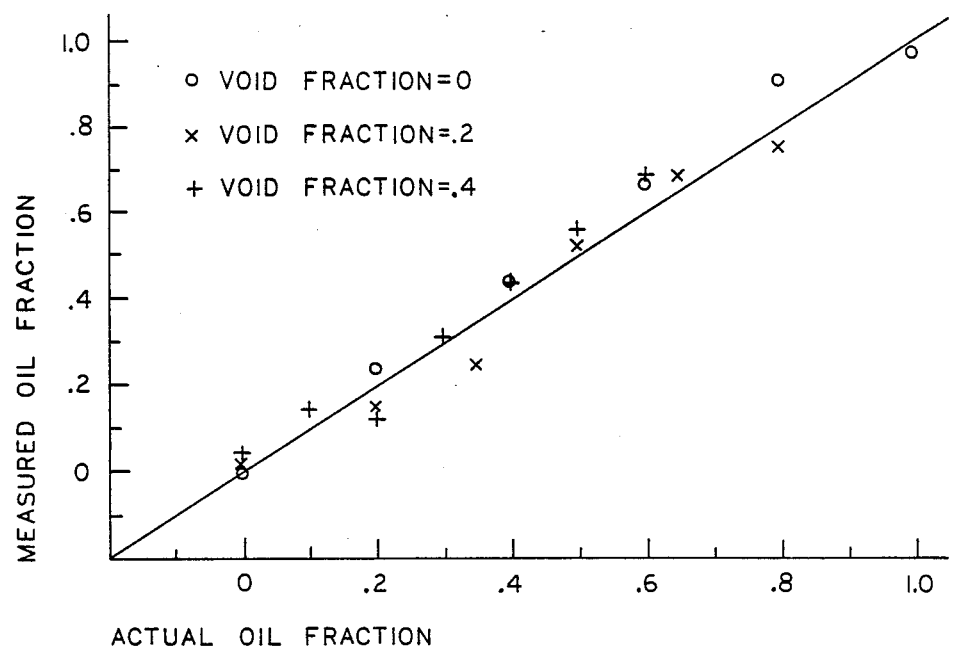
FIGS. 12 and 13 show the results of a test in which the alternate embodiment of the present invention was used to determine the oil fraction and void fraction in a range of known oil/water/air samples.
Figure 13:
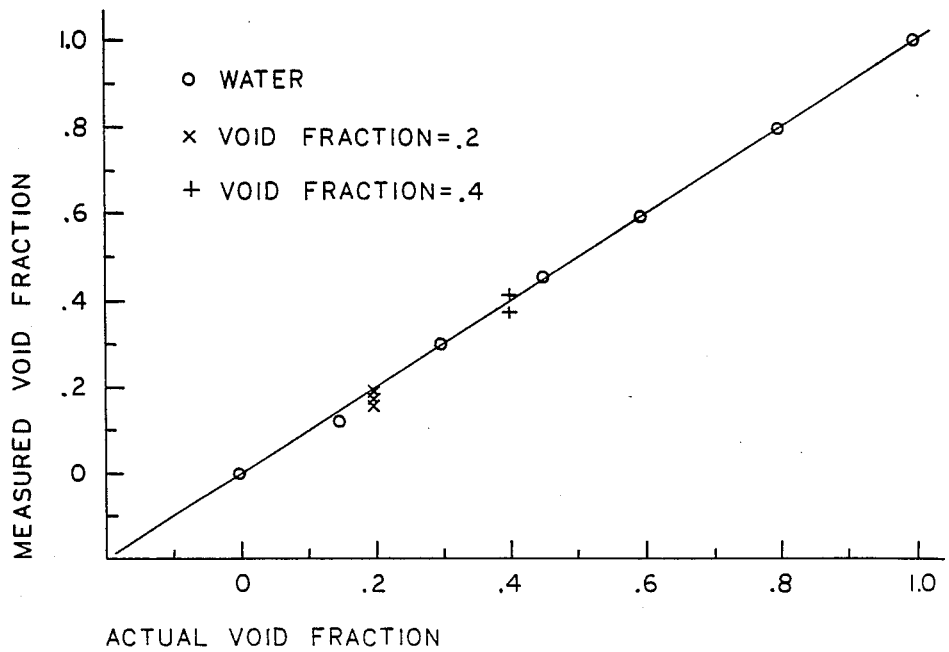

The accuracy of this method was tested by using it to measure the oil and air fractions in various known oil-water-air mixtures. The results of these tests are given in FIGS. 12 and 13. It can readily be observed that the agreement between the measured and the actual values is reasonable over a wide range of mixtures.

In the two methods described herein of practicing the present invention the hydrogen density of the oil was substantially equal to that of the water. This simplifies the determination of the volume fractions of the flowstream constituents. Where the hydrogen density of the oil differs significantly from that of water, it may be necessary to modify the method to accommodate this difference. For example, in the second embodiment of present invention a difference between the hydrogen densities of oil and water would be accommodated by using the following equation to determine the value of $(A_{hs})_f$ in equation 3:

$$(A_{hs})_f = (A_{hs})_o \times Y_o + (A_{hs})_w \times (1 - Y_o) \qquad \text{eqn. 10}$$

where $Y_o = \dfrac{\alpha_o}{\alpha_o + \alpha_w}$

An approximation is first made of the oil and water volume fractions and equation 10 is used to determine the value of $(A_{hs})_f$ based on this approximation. Equations 3–9 are then applied to yield an approximation of the oil, water and air volume fractions. These values for the oil and water volume fractions are then applied in equation 10 to yield an improved value for $(A_{hs})_f$ and the procedure is then repeated in a recursive manner until the approximations of the oil and water volume fractions converge on their final values.

The preferred embodiment of the present invention and the best known modes of practicing it have been detailed above. Clearly, numerous improvements and modifications could be made without departing from the scope of the invention set forth in the following claims.

We claim:

1. A method for monitoring a mixture of oil, water and gas flowing through a conduit, comprising the steps of:

introducing into the flowstream a population of fast neutrons generated by a chemical fast neutron source, said source being substantially free of Beryllium and adapted to gene rate gamma radiation having at least one gamma peak at X MeV, X being greater than the 4.43 Mev $C^{12}$ inelastic scattering gamma peak;

monitoring the gamma emanating from said mixture to establish a first gamma count rate for a range of gamma energies above about X MeV, whereby the first gamma count rate represents the simultaneous detection of the 2.2 Mev $C^{12}$ inelastic scattering gamma plus the source gamma at X MeV plus background; and comparing the first gamma count rate of an empirical relationship between the count rate and gas fraction to establish the relative amount of gas within the conduit.

2. The method as set forth in claim 1 wherein said range of gamma energies extends from about 6.2 MeV to about 8.0 MeV.

3. The method as set forth in claim 1 wherein said range of gamma energies extends from about 6.4 MeV to about 8.0 MeV.

4. The method as set forth in claim 1 further comprising the steps of:

monitoring the gamma spectrum to establish a second gamma count rate corresponding to gamma emissions falling within the range of gamma energies corresponding to inelastic neutron scattering from $C^{12}$ nuclides; and comparing the second gamma count rate to an empirical relationship between the count rate and the oil fraction to determine the relative amount of oil with the oil-water mixture.

5. The method as set forth in claim 4 wherein establishing said second gamma count rate includes the step of determining the net $C^{12}$ inelastic scattering gamma count rate.

6. The method as set forth in claim 4 further comprising the steps of:

monitoring the gamma spectrum to establish a third gamma count rate corresponding to gamma emissions falling within the range of energies corresponding to inelastic neutron scattering from $O^{16}$; and normalizing at least one of said first and second count rates based on said third gamma count rate.

7. The method as set forth in claim 1 wherein the neutron source is a $C^{13}$-$Pu^{238}$ source.

8. A method for monitoring a mixture of oil, water and gas flowing through a conduit, comprising the steps of:

introducing into the flowstream a population of fast neutrons, at least 5% of said neutrons having an energy in excess of 4.4 MeV;

monitoring the gamma spectrum emanating from said mixture to establish a first gamma count rate for a range of gamma energies above about 6.2 MeV;

comparing the first gamma count rate to an empirical relationship between the count rate and gas fraction to establish the relative amount of gas within the conduit;

monitoring the gamma spectrum to establish a second gamma count rate corresponding to gamma emissions falling within the range of gamma energies corresponding to inelastic neutron scattering from $C^{12}$ nuclides;

comparing the second gamma count rate to an empirical relationship between the count rate and the oil fraction to determine the relative amount of oil within the oil-water mixture; and monitoring the gamma spectrum to establish a third gamma count rate corresponding to gamma emissions falling within the range of energies corresponding to inelastic neutron scattering from $O^{16}$; wherein at least one of said first and second count rates is normalized based on said third gamma count rate.

* * * * *